United States Patent
Op De Beek et al.

(10) Patent No.: US 6,704,388 B2
(45) Date of Patent: Mar. 9, 2004

(54) X-RAY EXAMINATION APPARATUS

(75) Inventors: Johannes Catharina Antonius Op De Beek, Eindhoven (NL); Matheus Wilhelmus Kerkhof, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 10/022,125

(22) Filed: Oct. 30, 2001

(65) Prior Publication Data
US 2002/0080909 A1 Jun. 27, 2002

(30) Foreign Application Priority Data
Nov. 2, 2000 (EP) .............................. 00203827

(51) Int. Cl.⁷ ................................ G21K 1/12
(52) U.S. Cl. ..................... 378/18; 378/207; 250/252.1
(58) Field of Search ........................ 378/18, 207, 51, 378/53, 56, 4, 19; 250/252.1, 367

(56) References Cited
U.S. PATENT DOCUMENTS 5,301,108 A * 4/1994 Hsieh ............................ 378/8
6,148,057 A * 11/2000 Urchuk et al. .............. 378/207
2003/0043960 A1 * 3/2003 Op De Beek et al. ........ 378/19

* cited by examiner

Primary Examiner—Edward J. Glick
Assistant Examiner—Irakli Kiknadze
(74) Attorney, Agent, or Firm—John Vodopia

(57) ABSTRACT

An X-ray examination apparatus includes an X-ray source (1) for emitting an X-ray beam (8) having a central X-ray extending along a central beam line (4). There is also provided an X-ray detector (2) for picking up X-ray images. The X-ray source (1) and the X-ray detector (2) are rotatable together around an axis of rotation (3). The X-ray examination apparatus is provided with a calibration system (6, 7). Calibration images of the calibration phantom (6) are formed from different, preferably opposed directions of the X-ray beam (8). The zero orientation of the X-ray source (1) with the X-ray detector (2) is derived from differences in positions of the same aspect of the calibration phantom in the respective calibration images. The central beam line (4) extends perpendicularly to the axis of rotation (3) in the zero orientation.

5 Claims, 3 Drawing Sheets

X-RAY EXAMINATION APPARATUS

BACKGROUND OF THE INVENTION

Figure 1:
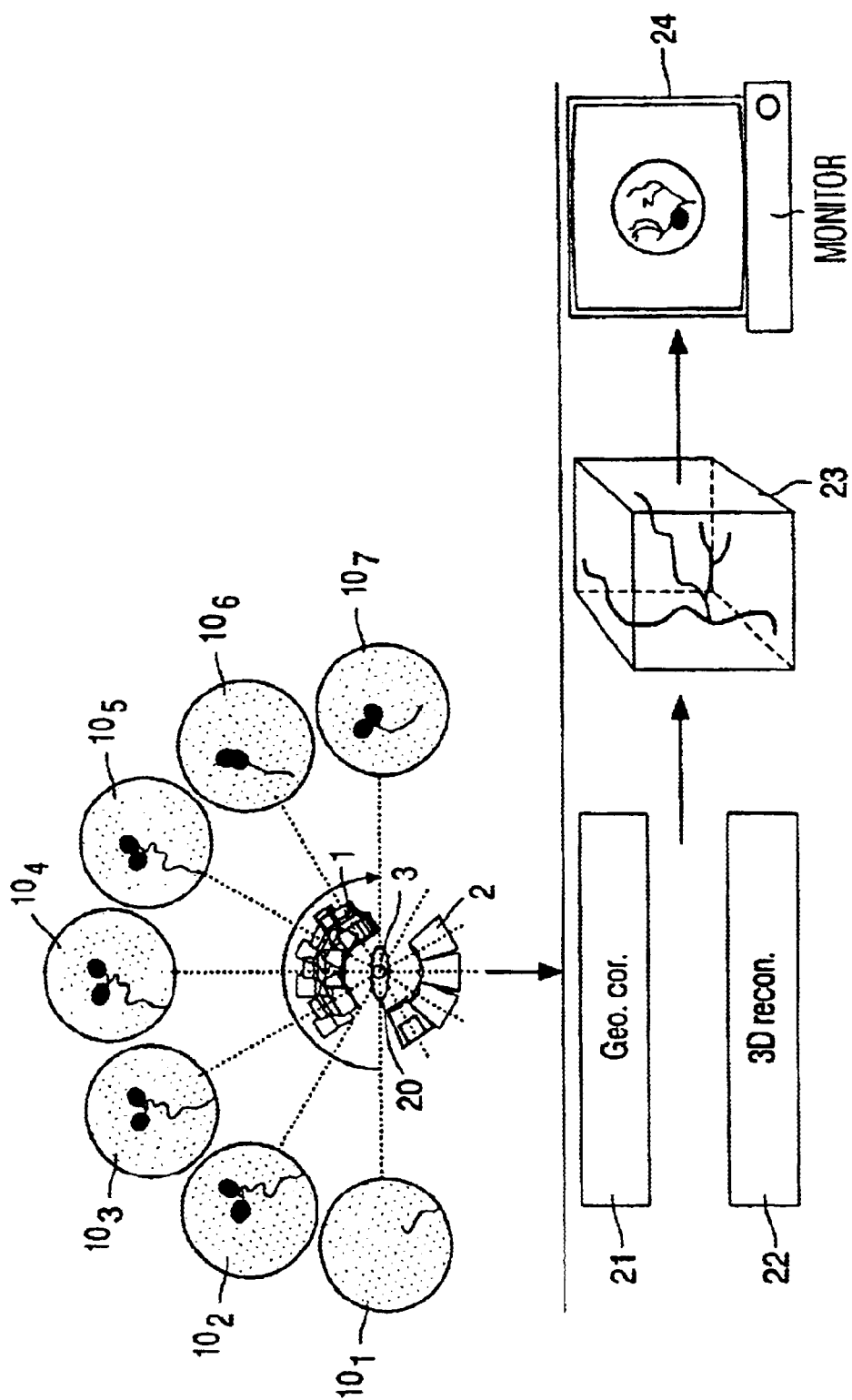

The invention relates to an X-ray examination apparatus which includes
an X-ray source for emitting an X-ray beam having a central X-ray extending along a central beam line, and
an X-ray detector for picking up X-ray images, where
   the X-ray detector and the X-ray source are rotatable together about an axis of rotation.

An X-ray examination apparatus of this kind is known from British patent application GB 2 315 395.

The known X-ray examination apparatus is used to form X-ray images of an object to be examined from a variety of directions. Each individual X-ray image depicts the object from a separate orientation. Display of the X-ray images in rapid succession for successive orientations creates the impression of a spatial rendition of the object to be examined. The known X-ray examination apparatus is not suitable for forming a real three-dimensional data set of the object to be examined.

OBJECTS AND SUMMARY OF THE INVENTION

It is an object of the invention to provide an X-ray examination apparatus which enables accurate reconstruction of a three-dimensional data set of the object from X-ray images for various orientations. Such a three-dimensional data set associates density values with positions in the three-dimensional geometrical space.

This object is achieved by means of an X-ray examination apparatus in accordance with the invention which includes a calibration system which is provided with
   a calibration phantom, and
a calibration control unit which is arranged
   to form separate calibration images for different, notably essentially opposed directions of the X-ray beam, and
   to determine the zero orientation of the X-ray source with the X-ray detector from differences between the positions in the individual calibration images of the same aspect of the calibration phantom reproduced, where
   the central beam line extends perpendicularly to the axis of rotation in the zero orientation.

Accurate calibration of the zero orientation is necessary for accurate reconstruction of the three-dimensional data set of the object to be examined, for example a patient to be examined. In the zero orientation the central beam line of the X-ray beam extends perpendicularly to the axis around which the X-ray source and the X-ray detector rotate together about the patient to be examined. The X-ray source is arranged to emit a cone-shaped or fan-shaped X-ray beam. The central beam line is the longitudinal symmetry axis of the X-ray beam. Accurate adjustment of the orientation of the X-ray source and the X-ray detector while the central beam line extends perpendicularly to the axis of rotation makes it possible to ensure that the central beam line and hence the central ray in the X-ray beam rotates accurately in one flat plane during rotation of the X-ray source together with the X-ray detector about the axis of rotation. It is thus possible to reconstruct the three-dimensional data set from the X-ray images in the various orientations, without introducing artefacts, while utilizing known reconstruction algorithms developed in computed tomography. In accordance with the invention it is notably possible to avoid artefacts in the form of so-called "streaks" and unsharpness in the 3D data set. Accurate adjustment of the orientation of the X-ray source and the X-ray detector so that the central beam line extends perpendicularly to the axis of rotation notably makes it possible to avoid rolling of the central beam line along a surface of cone when the X-ray source with the X-ray detector are rotated about the axis of rotation. In the case of such a displacement of the central ray across the surface of cone very complex reconstruction algorithms have to be used, provided that accurate reconstruction is possible at all.

Reconstruction algorithms for reconstructing the three-dimensional data set from the two-dimensional projection images formed by the X-ray images in different orientations are known per se from the article "Practical cone beam algorithms" in J. Opt. Soc. Am. A6(1984), pp. 612 to 619, by L. A. Feldkamp et al. Results obtained by means of such an algorithm are stated in the article "3D rotational angiography: clinical value in endovascular treatment" in Medica Mundi 43(1998), pp. 8 to 14, by J. Moret et al. It has notably been found that a three-dimensional reconstruction of the vascular system of the patient to be examined can be formed from two-dimensional subtraction projection images. This application is also referred to as 3D rotational angiography.

In accordance with the invention calibration images of the calibration phantom are formed from essentially opposed directions. Inter alia a deviation in the perpendicular orientation of the central beam line relative to the axis of rotation causes slight deviations of the exactly opposed directions occur. It has been found that such deviations, even though they are small per se, lead to considerable artefacts in the reconstructed three-dimensional data set. When the calibration images have been formed from exactly opposed directions of the central ray, the same aspect of the calibration phantom is imaged in the same position in both calibration images. A deviation between the position in which the relevant aspect is imaged in the two calibration images represents an accurate measure of the deviation of the central beam line from the normal to the axis of rotation. On the basis of this deviation the X-ray source and the X-ray detector can be readily displaced in such a manner that the central beam line extends perpendicularly to the axis of rotation.

An X-ray examination apparatus in accordance with the invention is particularly suitable for use in cardiological applications of radiology. A three-dimensional reconstruction of the heart of the patient to be examined is thus formed.

These and other aspects of the invention will be elaborated on the basis of the following embodiments which are defined in the dependent claims.

Preferably, the calibration phantom is situated outside the isocenter, even preferably as far as possible from the isocenter, that is, near the X-ray source or the X-ray detector. The isocenter is situated at the point of intersection of the central beam line and the axis of rotation. In this position a small deviation in respect of the perpendicular orientation of the central beam line relative to the axis of rotation gives rise to a large difference between the positions in which the relevant aspect is reproduced in the calibration images. A high sensitivity in respect of small deviations can thus be achieved.

Preferably, the calibration images are symmetrically masked from two sides. This can be realized, for example, by partly suppressing the electronic image signals representing the calibration images in such a manner that the suppressed parts are symmetrically situated relative to the center of each of the calibration images. The location where the relevant aspect of the calibration phantom is reproduced can be readily found in the images thus masked. It can notably be simply established whether and how far the relevant aspect of the calibration phantom is imaged from the center of the calibration image. The user himself, for example, can see whether the relevant aspect is imaged at the center of the calibration image; however, such positioning can also be detected by automatic image processing.

A ruler with a scale graduation is preferably used as the calibration phantom. The scale graduation has an X-ray absorption which deviates from that of the remainder of the ruler, so that the scale graduation can be clearly reproduced by means of X-rays. Such a ruler is readily visible in the calibration images. Suitable results are obtained notably by means of an X-ray transparent ruler whose graduation strokes and digits are made of lead; such a ruler is also referred to as a "lead ruler". A graduation stroke with an associated digit indication on the ruler is preferably used as the aspect on the basis of which the orientation of the central beam line is determined.

Other objects can also be used as a calibration phantom and readily recognizable elements of the phantom are suitable for use as the aspect on the basis of which the calibration is performed in accordance with the invention.

BRIEF DESCRIPTION OF THE DRAWING FIGURES

Figure 2:
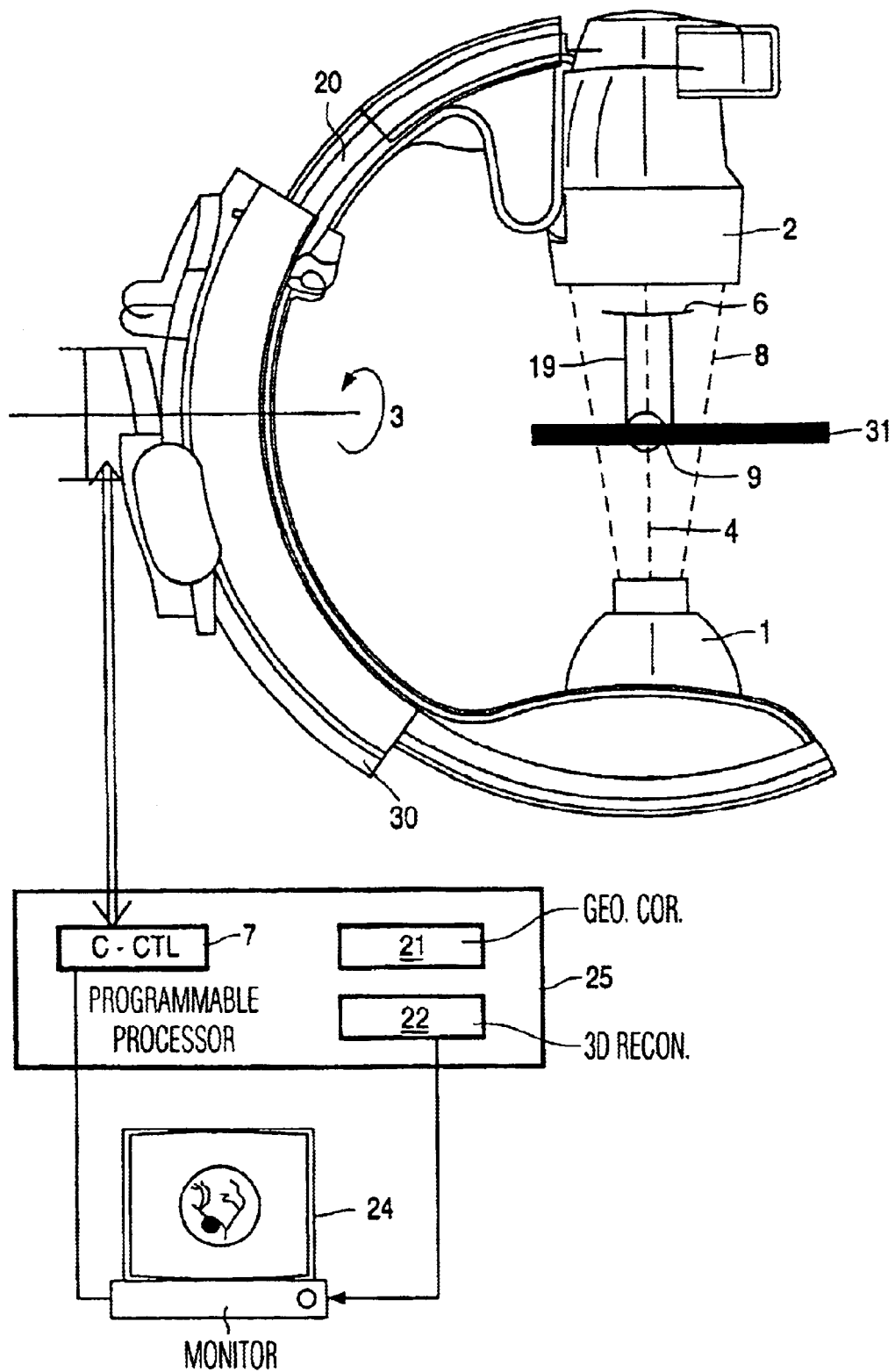
Figure 3:
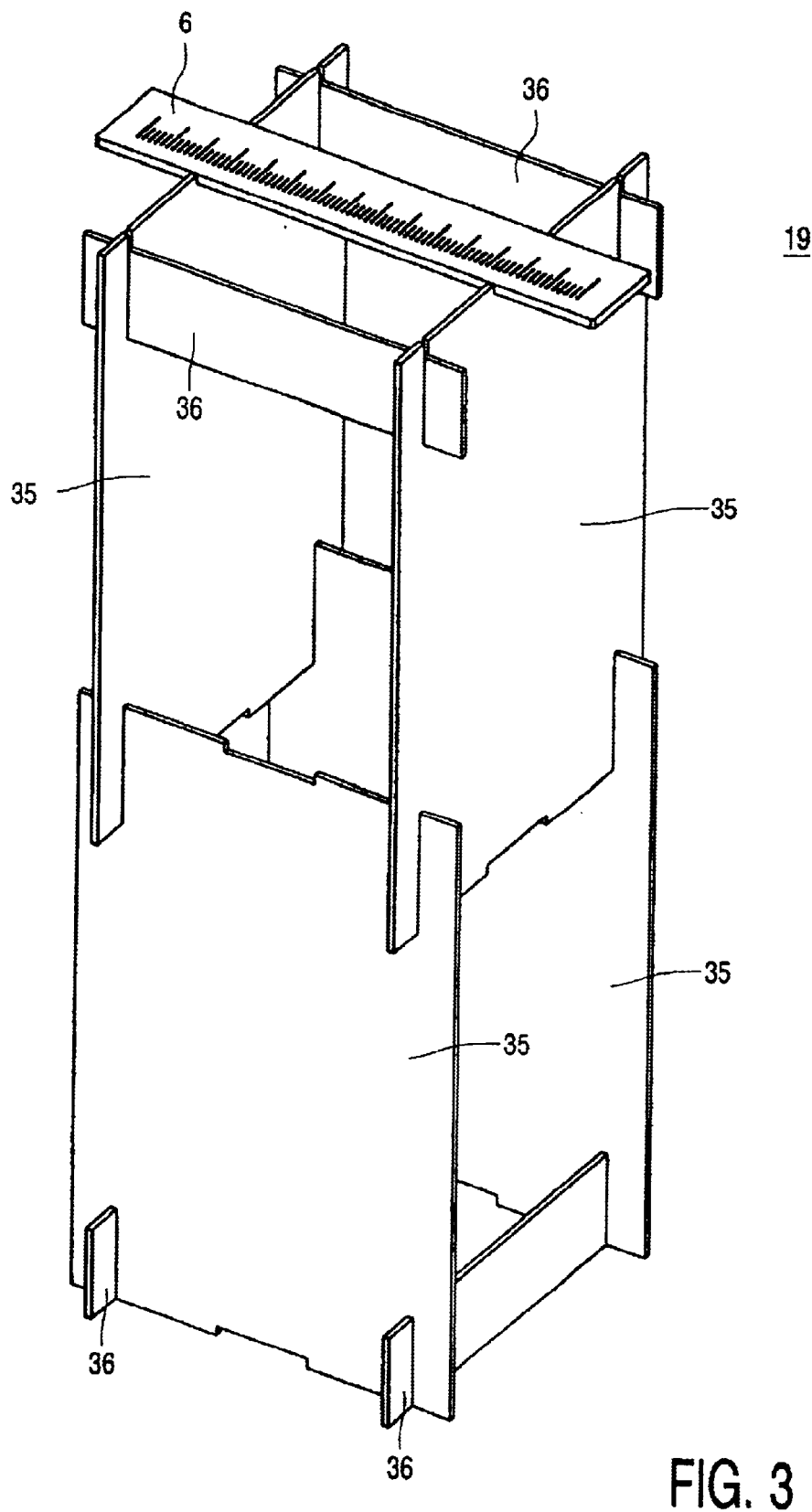

These and other aspects of the invention will be described in detail hereinafter, by way of example, with reference to the following embodiments and the accompanying drawing; therein:

FIG. 1 shows diagrammatically a set-up of the 3D rotation angiography procedure, FIG. 2 shows diagrammatically an X-ray examination apparatus in which the invention is used, and FIG. 3 shows the composition of a tower for the calibration phantom.

DETAILED DESCRIPTION OF THE DRAWING FIGURES

FIG. 1 is a diagrammatic representation of the 3D rotation angiography procedure. FIG. 1 shows the X-ray source I and the X-ray detector 2 in a number of orientations relative to the patient 20 to be examined. As is indicated by the arrow, the X-ray source and the X-ray detector are rotated together about the axis of rotation 3. To this end, for example, the X-ray source and the X-ray detector are both suspended from a support such as a C-arm 20. A two-dimensional projection image 101-107 is formed in each of said orientations. Such projection images are often subtraction images obtained by subtracting a current projection image from a previously picked up mask image, so that the subtraction image represents practically only the difference between the current projection image and the mask image. A number of geometrical corrections is applied to the projection images $10_1$-$10_7$ by means of a correction unit 21 in order to correct the projection images for known image distortion such as barrel and cushion distortion which occurs notably when an X-ray image intensifier with a television camera is used as the X-ray detector. The three-dimensional data set 23 is reconstructed from the projection images $10_1$-$10_7$ by means of a reconstruction unit 22. This three-dimensional data set is displayed, for example on a monitor 24 which is suitable for the (quasi) spatial display of the three-dimensional data set.

FIG. 2 shows diagrammatically an X-ray examination apparatus in which the invention is used. The X-ray source 1 and the X-ray detector 2, in this case being constructed as an X-ray image intensifier, are suspended from a support which is in this case a C-arm 20. The C-arm 20 is displaceable in a sleeve 30 while the X-ray source 1 and the X-ray detector 2 rotate together in the plane of drawing. This motion is also referred to as a rolling rotation. The sleeve 30 is also rotatable about the axis of rotation 3, the X-ray source 1 with the X-ray detector 2 then rotating in a plane transversely of the plane of drawing; the latter rotation is also referred to as a "propeller motion". Notably for cardiology such a propeller motion offers the possibility of performing a three-dimensional reconstruction of a high diagnostic quality of the heart of the patient to be examined.

The calibration phantom 6 is arranged on a tower 19 in order to carry out the calibration in accordance with the invention. The tower 19 is placed on the patient table 31. The calibration phantom is thus positioned outside the isocenter 9 and near the X-ray image intensifier 2 in the situation shown. An X-ray image, being the first calibration image of the calibration phantom, is formed under the control of the calibration control unit 7. Subsequently, again under the control of the calibration control unit 7, the C-arm 20 is rotated 180° about the axis of rotation 3; the positions of the X-ray source 1 and the X-ray detector 2 are thus reversed and the calibration phantom 6 is situated nearer to the X-ray source in comparison with the isocenter 9. Under the control of the calibration control unit 7 another X-ray image, being the second calibration image, is formed of the phantom. Inspection of the two calibration images so as to establish whether the image of the calibration phantom has relatively shifted reveals whether the central beam line 4 extends exactly perpendicularly to the axis of rotation 3. This can be done with the naked eye by displaying the two calibration images on the monitor 24.

In a contemporary X-ray examination apparatus the calibration control unit 7 and the correction unit 21 with the reconstruction unit 22 are usually included in a programmable processor 25. For example, the result of the calibration, being the zero orientation, can be stored in a memory of, for example the calibration control unit. The zero orientation can thus be easily fetched again.

FIG. 3 illustrates the building up of the tower for the calibration phantom. The tower 19 is preferably constructed while using a plurality of stacked, mating building elements which are known, for example from the toy industry. When the tower is not in use, it can be simply taken apart and stowed away without occupying a large storage volume. In that case the tower will not be in the way when it is not used after the calibration. Notably the upper building element is provided with a recess in which the calibration phantom, such as the lead ruler 6, can be accurately fitted. The simplest procedure is to provide all building elements with such a recess so that it will not be necessary to find exactly the upper building element upon assembly of the tower. It has been found in practice that suitable results are obtained by means of a tower which has a height of 36 cm and is composed of four large Perspex structural elements 35 and four small Perspex structural elements 36.

What is claimed is:

1. An X-ray examination apparatus which includes
   an X-ray source (1) for emitting an X-ray beam (8) having a central X-ray extending along a central beam line (4), and
   an X-ray detector (2) for picking up X-ray images, where the X-ray detector (2) and the X-ray source (1) are rotatable together about an axis of rotation (3), and a calibration system (6, 7) which is provided with
a calibration phantom (6) and
a calibration control unit (7) which is arranged
to form separate calibration images for different, notably essentially opposed directions of the X-ray beam, and
to determine the zero orientation of the X-ray source with the X-ray detector from differences between the positions in the individual calibration images of the same aspect of the imaged calibration phantom, where
the central beam line (4) extends perpendicularly to the axis of rotation (3) in the zero orientation.

2. An X-ray examination apparatus as claimed in claim 1, wherein the axis of rotation and the central beam line intersect in an isocenter (9), and
wherein the calibration phantom is positioned outside the isocenter so as to form the calibration X-ray images.

3. An X-ray examination apparatus as claimed in claim 2, wherein the distance between the isocenter and the calibration phantom during the formation of at least one of the calibration X-ray images is larger than the distance between the X-ray detector and the calibration phantom.

4. An X-ray examination apparatus as claimed in claim 1, wherein
the X-ray detector is arranged to derive electronic calibration image signals from the calibration X-ray images,
the calibration control unit is arranged to suppress electronic parts of the electronic calibration image signals, the suppressed parts being situated symmetrically relative to the center of the calibration images, and
to display masked calibration images on the basis of the partly suppressed electronic image signals and to calibrate the zero orientation on the basis of the masked calibration images.

5. An X-ray examination apparatus as claimed in claim 1, wherein the calibration system includes a tower with a plurality of mating structural elements for supporting the calibration phantom.

* * * * *